(12) United States Patent
Kiessling

(10) Patent No.: US 12,171,595 B2
(45) Date of Patent: Dec. 24, 2024

(54) COMPUTED TOMOGRAPHY GANTRY WITH PROXIMITY SWITCH FOR DETECTING A ZERO POSITION

(71) Applicant: Siemens Healthcare GmbH, Erlangen (DE)

(72) Inventor: Florian Kiessling, Forchheim (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 250 days.

(21) Appl. No.: 17/886,534

(22) Filed: Aug. 12, 2022

(65) Prior Publication Data

US 2023/0046025 A1 Feb. 16, 2023

(30) Foreign Application Priority Data

Aug. 16, 2021 (DE) ...................... 20 2021 104 359.8

(51) Int. Cl.
*A61B 6/03* (2006.01)
*A61B 6/00* (2006.01)
*A61B 90/00* (2016.01)

(52) U.S. Cl.
CPC ............ *A61B 6/035* (2013.01); *A61B 6/4447* (2013.01); *A61B 90/06* (2016.02); *A61B 6/547* (2013.01); *A61B 2090/067* (2016.02); *A61B 2560/0462* (2013.01)

(58) Field of Classification Search
None
See application file for complete search history.

(56) References Cited

U.S. PATENT DOCUMENTS

| | | | | |
|---|---|---|---|---|
| 6,412,345 B1 * | 7/2002 | Murray | ................... | G01M 1/32 73/462 |
| 6,508,586 B2 * | 1/2003 | Oota | ...................... | A61B 6/467 378/194 |
| 7,806,590 B2 * | 10/2010 | Jimbo | .................. | A61B 6/4488 378/4 |
| 8,842,804 B2 * | 9/2014 | Ooshima | ................ | A61B 6/027 378/20 |

(Continued)

FOREIGN PATENT DOCUMENTS

| | | | | |
|---|---|---|---|---|
| CN | 1946343 B | * | 9/2011 | ............. A61B 6/032 |
| CN | 112494060 A | * | 3/2021 | ............. A61B 6/032 |

OTHER PUBLICATIONS

English translation of CN 112494060 A (Year: 2021).*
English translation of CN 1946343 B (Year: 2011).*

*Primary Examiner* — Thomas R Artman
(74) *Attorney, Agent, or Firm* — Harness, Dickey & Pierce, P.L.C.

(57) ABSTRACT

In a gantry for a computed tomography device, a rotary frame is arranged on the tilt frame so that the rotary frame rotates relative to the tilt frame about an axis of rotation. The tilt frame is arranged on the support frame so that the tilt frame tilts about a tilt axis relative to the support frame, such that a tilt angle of the tilt frame relative to the support frame is changeable by a tilting movement of the tilt frame relative to the support frame about the tilt axis. The proximity switch has a proximity sensor and a reference mark, which interacts with the proximity sensor. The proximity switch is also coupled to the support frame and to the tilt frame such that the proximity switch is configured to react to an approach of the tilt angle to a reference angle.

19 Claims, 4 Drawing Sheets

(56) References Cited

U.S. PATENT DOCUMENTS

| | | | | |
|---|---|---|---|---|
| 8,985,852 | B2* | 3/2015 | Theiss | A61B 6/035 |
| | | | | 378/197 |
| 10,788,321 | B2* | 9/2020 | Honea | G01C 3/08 |
| 2002/0039403 | A1* | 4/2002 | Oota | A61B 6/032 |
| | | | | 378/4 |
| 2009/0232281 | A1* | 9/2009 | Jimbo | A61B 6/4488 |
| | | | | 378/199 |
| 2012/0177172 | A1* | 7/2012 | Ooshima | A61B 6/547 |
| | | | | 378/4 |
| 2014/0016758 | A1* | 1/2014 | Theiss | A61B 6/035 |
| | | | | 378/197 |
| 2019/0265030 | A1* | 8/2019 | Honea | G01S 17/08 |
| 2023/0046025 | A1* | 2/2023 | Kiessling | A61B 6/4441 |

* cited by examiner

COMPUTED TOMOGRAPHY GANTRY WITH PROXIMITY SWITCH FOR DETECTING A ZERO POSITION

CROSS-REFERENCE TO RELATED APPLICATION(S)

The present application claims priority under 35 U.S.C. § 119 to German Patent Application No. 20 2021 104 359.8, filed Aug. 16, 2021, the entire contents of which are incorporated herein by reference.

BACKGROUND

In computed tomography devices (CT devices) that are fitted with a tiltable frame the accuracy required for image reconstruction means that it is frequently necessary to detect the tilt angle, using a sensor system for example. The detection of the tilt angle can take place in a variety of ways and can in particular be aligned to the control and/or the actuating elements of the tilt drive used.

In this case a zero position is relevant for most applications in this context, the tilt angle being equal to a reference angle in said zero position. Particular scan modes can be available for the zero position, and call for a high level of precision in respect of the detection of the zero position.

SUMMARY

An object of one or more example embodiments of the present invention is to provide an alternative to the conventional detection of the zero position of the tilt frame for a gantry of a computed tomography device.

One or more example embodiments of the present invention relates to a gantry for a computed tomography device,
wherein the gantry has a support frame, a tilt frame, a tilt bearing, a rotary frame, a rotary bearing and a proximity switch,
wherein the rotary frame is arranged on the tilt frame so that via the rotary bearing it can rotate about an axis of rotation relative to the tilt frame,
wherein the tilt frame is arranged on the support frame so that via the tilt bearing it can tilt about a tilt axis relative to the support frame, such that a tilt angle of the tilt frame can be changed relative to the support frame by a tilting movement of the tilt frame relative to the support frame about the tilt axis, in particular in respect of an angular width of the tilt angle,
wherein the proximity switch has a proximity sensor and a reference mark which interacts with the proximity sensor, in particular interacts contactlessly,
wherein the proximity switch is coupled to the support frame and to the tilt frame such that the proximity switch reacts when the tilt angle approaches a reference angle.

The approach of the tilt angle to the reference angle takes place in this case on the basis of the tilting movement of the tilt frame relative to the support frame. The consequent approach of the reference mark to the proximity sensor can be detected via the proximity switch.

In particular, it can be provided that a vertex of the tilt angle and of the reference angle lies on the tilt axis and/or that the tilt angle and the reference angle lie in a plane perpendicular to the tilt axis. The tilt angle can in particular be an angle between the axis of rotation and a reference plane. The reference plane can in particular be horizontal. The position of the tilt frame relative to the support frame, in which the tilt angle is equal to the reference angle, can also be referred to as the zero position.

One form of embodiment provides that the axis of rotation is horizontal when the tilt angle is equal to the reference angle.

One form of embodiment provides that the proximity switch has a reference area with a first sub-area and a second sub-area, which are arranged consecutively in respect of an angular distance about the tilt axis, wherein the reference mark is arranged in respect of the angular distance about the tilt axis between the first sub-area and the second sub-area.

In particular, it can be provided that the first sub-area and the second sub-area differ in respect of interaction with the proximity sensor such that the proximity switch assumes a first signal status when in respect of the angular distance about the tilt axis the proximity sensor is situated closer to the first sub-area than to the second sub-area, and that the proximity switch assumes a second signal status, which differs from the first signal status, when in respect of the angular distance about the tilt axis the proximity sensor is situated closer to the second sub-area than to the first sub-area.

In particular, the proximity switch can be designed to be two-pole, such that it can switch from the first signal status to the second signal status when a corresponding first movement of the reference mark and of the proximity sensor relative to one another takes place, and that it can switch from the second signal status to the first signal status when a corresponding second movement of the reference mark and of the proximity sensor relative to one another takes place.

Based on the signal status of the proximity switch a direction for the tilting movement can be determined, in order for the tilt angle to approach the reference angle. This can take place for example in an initialization process of the computed tomography device via a control unit of the computed tomography device.

One form of embodiment provides that the first sub-area is designed in the form of a first circular arc about a center of a circle, wherein the second sub-area is designed in the form of a second circular arc about the center of a circle, wherein the center of the circle lies on the tilt axis.

One form of embodiment provides that an edge of the first sub-area which adjoins the second sub-area forms the reference mark. In particular, it can be provided that the reference mark marks a border between the first sub-area and the second sub-area.

One form of embodiment provides that the gantry has a reference structure made of a material, to which the proximity switch reacts on the approach of said material to the proximity sensor, wherein the reference structure contains the first sub-area, wherein a recess is designed in the reference structure and forms the second sub-area.

The recess can for example be an opening or a depression or can consist of a material to which the proximity sensor does not react on the approach of said material. The reference structure can for example be designed to be flat and/or extend in a plane which is perpendicular to the tilt axis.

One form of embodiment provides that the material is sheet metal. The reference structure can in particular be a flat sheet metal contour.

The proximity switch can in particular be based on a contactless measurement principle and/or react to a contactless approach of the reference mark to the proximity sensor. For example, it can be provided that the proximity switch is a capacitive proximity switch.

One form of embodiment provides that the proximity switch is an inductive proximity switch. An inductive proximity switch reacts on the basis of the change in a magnetic field generated by the proximity sensor in response to an approach of a metal object to the proximity sensor. The inductive proximity switch can thus also react to an approach of a reference mark, which is designed in the form of an edge of a metal body, to the proximity sensor.

One form of embodiment provides that the proximity switch is an optical proximity switch, for example in the form of a light barrier.

One form of embodiment provides that the gantry has a tilt drive for driving the tilting movement of the tilt frame relative to the support frame about the tilt axis, wherein a distance of the proximity sensor and/or of the reference mark from the tilt axis is greater than a length of a lever arm of the tilt drive in respect of the tilt axis.

In particular, a distance of a rotary joint of the tilt drive, said rotary joint being coupled to the tilt frame, from the tilt axis is less than the distance of the proximity sensor and/or of the reference mark from the tilt axis.

Based on a relatively high distance of the proximity sensor and of the reference mark from the tilt axis, it is possible to achieve a relatively high level of accuracy with which the approach of the tilt angle to the reference angle can be detected, for example in an accuracy range which is less than 0.1°, in particular less than 0.05°.

One form of embodiment provides that the proximity sensor and the reference mark are arranged offset relative to one another in respect of a direction parallel to the tilt axis, wherein the proximity sensor and the reference mark are equally far distant from the tilt axis. The tilting movement of the tilt frame relative to the support frame thus causes a lateral movement of the reference mark and of the proximity sensor relative to one another.

One form of embodiment provides that the proximity sensor is fixedly arranged relative to the tilt frame and wherein the reference mark is fixedly arranged relative to the support frame. The proximity sensor can for example be fixedly arranged on the tilt frame. The reference mark and/or the reference area can for example be fixedly arranged on the support frame and/or be integrated into the support frame. For example, the support frame can have the reference structure.

One form of embodiment provides that the proximity sensor is fixedly arranged relative to the support frame and wherein the reference mark is fixedly arranged relative to the tilt frame. The proximity sensor can for example be fixedly arranged on the support frame. The reference mark and/or the reference area can for example be fixedly arranged on the tilt frame and/or be integrated into the tilt frame. For example, the tilt frame can have the reference structure.

The gantry can further for example have an inclination sensor, in order to determine an angular width of the tilt angle, in particular when the tilt angle differs from the reference angle. The inclination sensor can for example be fixedly arranged on the tilt frame. The inclination sensor can for example be based on a microelectromechanical system and/or be designed as an acceleration sensor.

The gantry can further for example have a rotary encoder, in order to determine an angular width of the tilt angle, in particular when the tilt angle differs from the reference angle. The rotary encoder can for example be arranged coaxially to the tilt axis, wherein the rotary encoder is directly coupled to the support frame and to the tilt frame. To increase the accuracy the rotary encoder can instead be coupled to a gear stage of the tilt drive.

One or more example embodiments of the present invention further relate to a computed tomography device, having an inventive gantry. One or more example embodiments of the present invention further relate to a use of the proximity switch in the inventive gantry, in order to detect the approach of the tilt angle to the reference angle.

Via the proximity switch an approach of the tilt angle to the reference angle can be detected with a relatively high level of measuring accuracy at relatively low cost. In particular, it is thus not necessary to use a costly and production-intensive configuration (e.g. vibration damping, complex calibration) to increase the measuring accuracy of a tilt angle measurement system based on inclination sensors for use when detecting the zero position.

Within the scope of the present invention, features that are described in respect of different forms of embodiments of the present invention and/or different claim categories (method, use, apparatus, system, arrangement, etc.) can be combined to form further forms of embodiment of the present invention. For example, a claim that relates to an apparatus can also be developed with features that are described or claimed in connection with a method, and vice versa. Functional features of a method can in this case also be executed using correspondingly designed representational components.

The use of the indefinite article "a" or "an" does not rule out that the feature in question may also be present multiple times. The use of the expression "unit" does not rule out that the object to which the expression "unit" refers may have multiple components which are spatially separated from one another.

BRIEF DESCRIPTION OF THE DRAWINGS

The present invention is explained below using exemplary embodiments with reference to the attached figures. The representation in the figures is schematic, greatly simplified and not necessarily true to scale.

DETAILED DESCRIPTION

Figure 1:
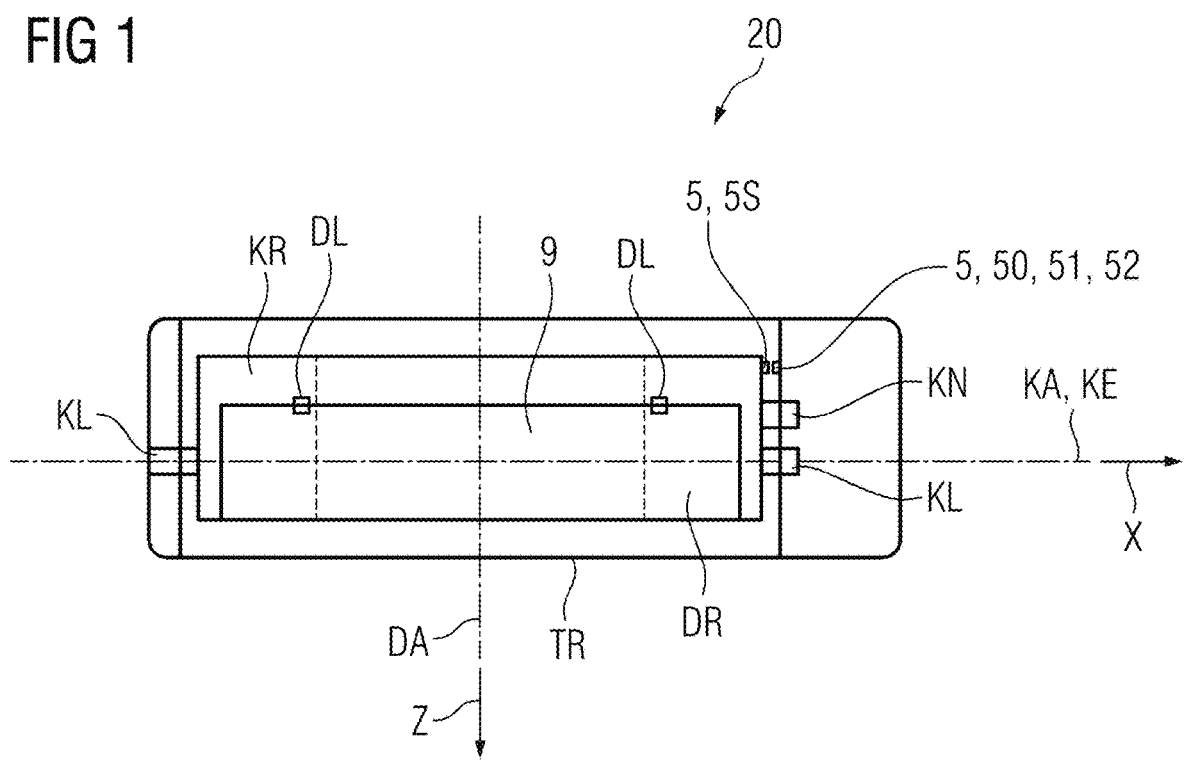
FIG. 1 shows a first view of a gantry for a computed tomography device.

FIG. 1 shows a first view of a gantry 20 for a computed tomography device 1, wherein the gantry 20 has a support frame TR, a tilt frame KR, a tilt bearing KL, a rotary frame DR, a rotary bearing DL and a proximity switch 5. The rotary frame DR is arranged on the tilt frame KR so that via the rotary bearing DL it can rotate about an axis of rotation DA relative to the tilt frame KR. The tilt frame KR is arranged on the support frame TR so that via the tilt bearing KL it can tilt about a tilt axis KA relative to the support frame TR, such that a tilt angle KW of the tilt frame KR relative to the support frame TR can be changed by a tilting movement of the tilt frame KR relative to the support frame TR about the tilt axis KA, in particular can be changed in respect of an angular width of the tilt angle KW.

The proximity switch 5 has a proximity sensor 5S and a reference mark 50 which interacts with the proximity sensor 5S, in particular interacts contactlessly. The proximity switch 5 is coupled to the support frame TR and to the tilt frame KR such that the proximity switch 5 reacts to an approach of the tilt angle KW to a reference angle RW. The proximity switch 5 is used to detect the approach of the tilt angle KW to the reference angle RW. The axis X is horizontal and parallel to the tilt axis KA.

Figure 2:
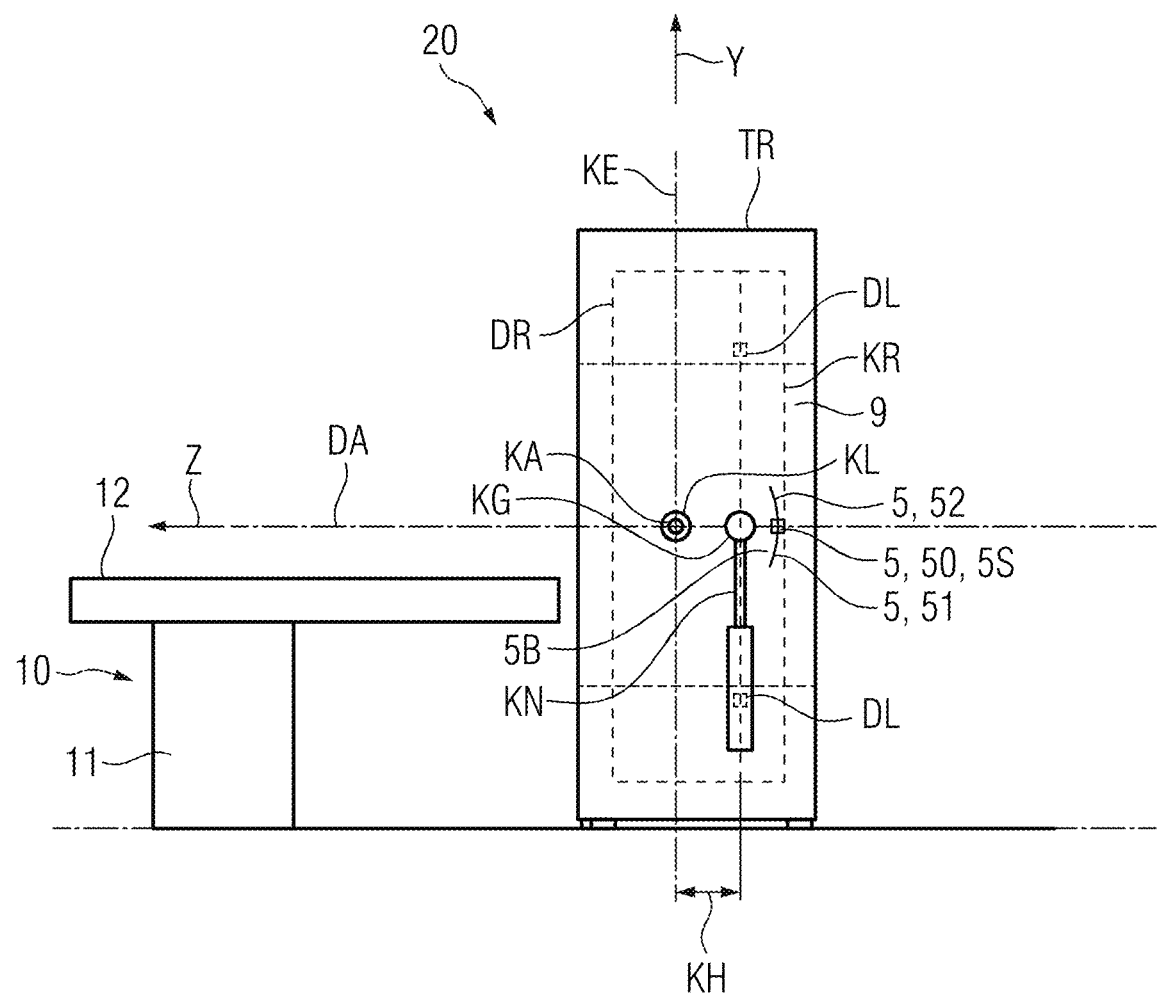
FIG. 2 shows a second view of a gantry for a computed tomography device.

FIG. 2 shows a second view of the gantry 20 for the computed tomography device 1, wherein the tilt frame KR is situated in the zero position relative to the support frame TR. The tilt angle KW is equal to the reference angle RW, such that the axis of rotation DA is horizontal and parallel to the axis Z. The scan plane is situated in the tilt plane KE, which contains the tilt axis KA and is perpendicular to the axis of rotation DA. The axis Y is vertical and perpendicular to the axis X. The axis Z is horizontal, perpendicular to the axis X and perpendicular to the axis Y.

The gantry 20 has a tilt drive KN for driving the tilting movement of the tilt frame KR relative to the support frame TR about the tilt axis KA. A distance of the proximity sensor 5S and of the reference mark 50 from the tilt axis KA is greater than a length of a lever arm KH of the tilt drive KN in respect of the tilt axis KA. The distance of the rotary joint KG of the tilt drive KN, which is coupled to the tilt frame KR, from the tilt axis KA is less than the distance of the proximity sensor 5S and of the reference mark 50 from the tilt axis KA. The distance of the proximity sensor 5S and of the reference mark 50 from the tilt axis KA can in particular be greater than 10 centimeters, for example greater than 20 centimeters.

The proximity sensor 5S and the reference mark 50 are arranged offset relative to one another in respect of the direction x parallel to the tilt axis KA. The proximity sensor 5S and the reference mark 50 are equally far distant from the tilt axis KA.

The proximity sensor 5S is fixedly arranged on the tilt frame KR relative to the tilt frame KR and the reference mark 50 is fixedly arranged relative to the support frame TR. The reference mark 50 and the reference area, which comprises the first sub-area 51 and the second sub-area 52, are integrated into the support frame TR. The support frame TR has the reference structure 5B.

Figure 3:
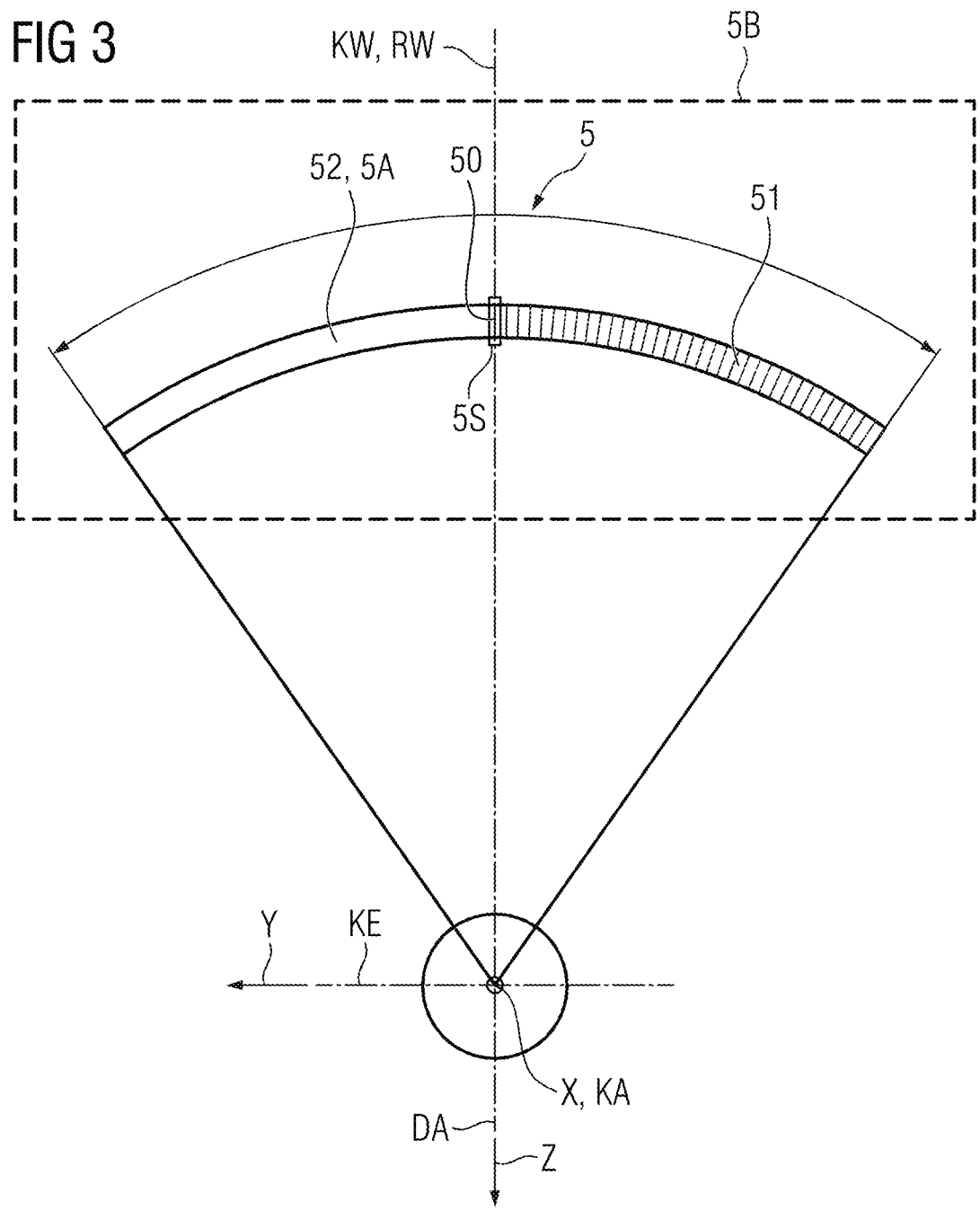
FIG. 3 shows a representation of the proximity switch relative to the tilt axis.

FIG. 3 shows a representation of the proximity switch 5 relative to the tilt axis KA. The proximity switch 5 has a reference area with a first sub-area 51 and a second sub-area 52, which are arranged consecutively about the tilt axis KA in respect of an angular distance, wherein the reference mark 50 is arranged in respect of the angular distance about the tilt axis KA between the first sub-area 51 and the second sub-area 52.

The first sub-area 51 and the second sub-area 52 differ in respect of interaction with the proximity sensor 5S, such that the proximity switch 5 assumes a first signal status when the proximity sensor 5S is closer to the first sub-area 51 than to the second sub-area 52 in respect of the angular distance about the tilt axis KA, and that the proximity switch 5 assumes a second signal status, which differs from the first signal status, when the proximity sensor 5S is situated closer to the second sub-area 52 than to the first sub-area 51 in respect of the angular distance about the tilt axis KA.

The first sub-area 51 is designed in the form of a first circular arc about a center of a circle. The second sub-area 52 is designed in the form of a second circular arc about the center of a circle. The center of the circle lies on the tilt axis KA. The edge of the first sub-area 51, which adjoins the second sub-area 52, forms the reference mark 50.

The gantry 20 has a reference structure 5B made of a material, to which the proximity switch 5 reacts on the approach of said material to the proximity sensor 5S. The reference structure 5B contains the first sub-area 51. A recess 5A which forms the second sub-area 52 is designed in the reference structure 5B.

Figure 4:
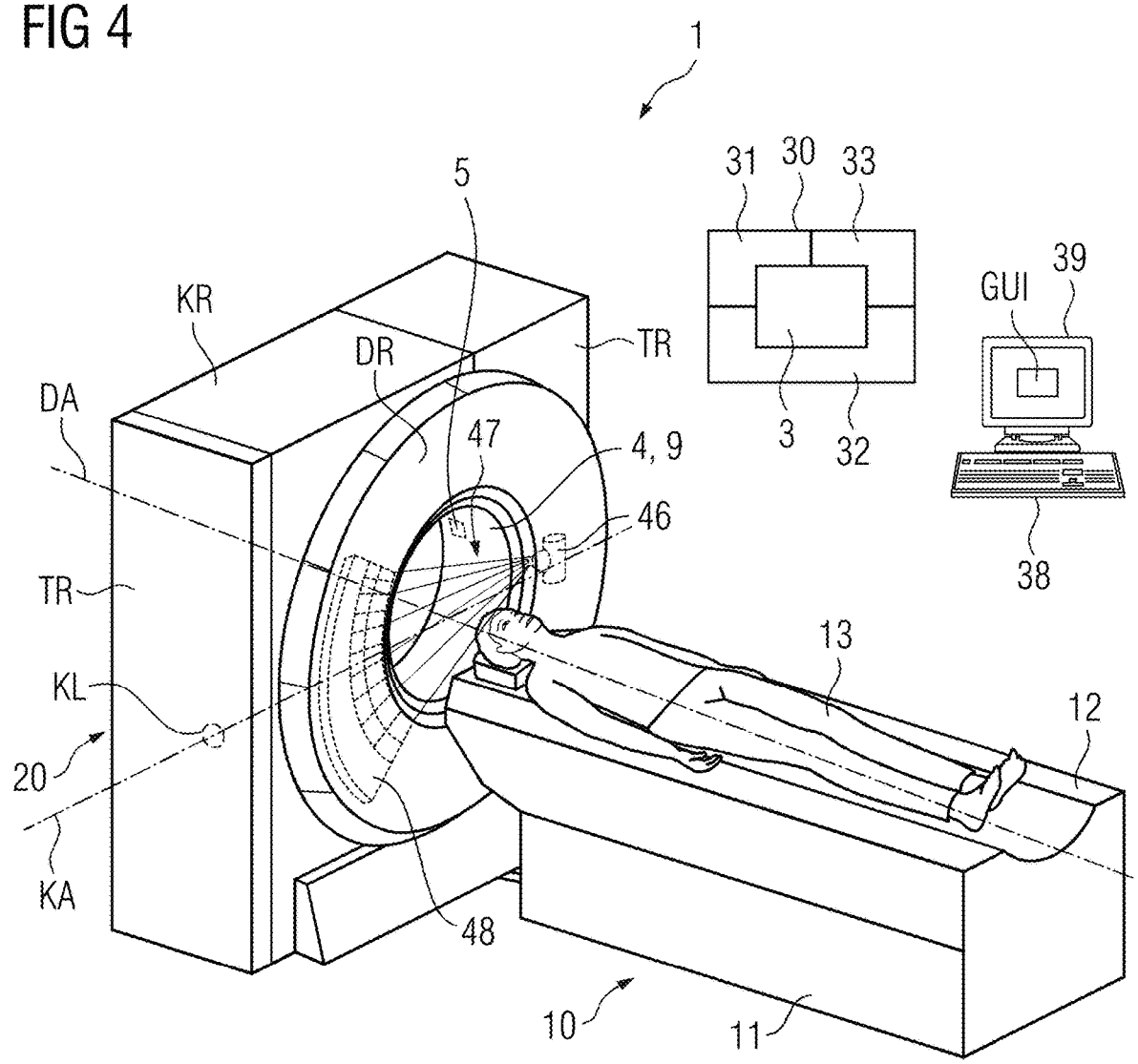
FIG. 4 shows a computed tomography device.

FIG. 4 shows a computed tomography device 1, having the gantry 20 and the data processing system 30. The rotary frame DR contains the X-ray tube 46 for generating the X-ray radiation 47 and the X-ray detector 48 for detecting the X-ray radiation 47.

The patient couch 10 has a couch base 11 and a couch bed 12, which is movably mounted relative to the couch base 11 in a longitudinal direction of the couch bed 12, such that the patient 13 lying on the couch bed 12 can be introduced into the tunnel-shaped opening 9, so that in the image data acquisition area 4 which is situated in the tunnel-shaped opening 9 an interaction can take place between a region of the patient 13 to be examined and the X-ray radiation 47. The longitudinal direction of the couch bed 12 is parallel to the axis Z.

The data processing system 30 has a processor 31, a memory unit 33 and a data transmission interface 32, which together form a control unit 3. The data processing system 30 can for example be designed in the form of a computer. The computed tomography device 1 further has an input unit 38 and an output unit 39 in the form of a monitor. The input unit 38 and the output unit 39 form a graphical user interface GUI, in which for example information relating to a signal status of the proximity switch 5 can be displayed and/or into which for example user input for controlling the computed tomography device 1, in particular the control unit 3 and/or the tilt drive KN, can be input.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

What is claimed is:

1. A gantry for a computed tomography device, the gantry comprising:
    a support frame;
    a tilt frame;
    a tilt bearing;
    a rotary frame;
    a rotary bearing; and
    a proximity switch;

wherein the rotary frame is arranged on the tilt frame and configured to rotate, via the rotary bearing, relative to the tilt frame about an axis of rotation;

wherein the tilt frame is arranged on the support frame and configured to tilt, via the tilt bearing, about a tilt axis relative to the support frame such that a tilt angle of the tilt frame relative to the support frame is changeable by a tilting movement of the tilt frame relative to the support frame, about the tilt axis;

wherein the proximity switch has a proximity sensor and a reference mark, the reference mark configured to interact with the proximity sensor;

wherein the proximity switch is coupled to the support frame and to the tilt frame such that the proximity switch is configured to react to an approach of the tilt angle to a reference angle;

wherein the proximity sensor and the reference mark are arranged offset relative to one another with respect to a direction parallel to the tilt axis; and wherein the proximity sensor and the reference mark are equally distant from the tilt axis.

2. The gantry as claimed in claim 1, wherein the axis of rotation is horizontal when the tilt angle is equal to the reference angle.

3. The gantry as claimed in claim 2,
wherein the proximity switch has a reference area with a first sub-area and a second sub-area, the first sub-area and the second sub-area arranged consecutively with respect to an angular distance about the tilt axis,
wherein the reference mark is arranged with respect to the angular distance about the tilt axis between the first sub-area and the second sub-area,
wherein the first sub-area and the second sub-area differ with respect to interaction with the proximity sensor such that the proximity switch assumes a first signal status when, with respect to the angular distance about the tilt axis, the proximity sensor is situated closer to the first sub-area than to the second sub-area, and such that the proximity switch assumes a second signal status, which differs from the first signal status, when, with respect to the angular distance about the tilt axis, the proximity sensor is situated closer to the second sub-area than to the first sub-area.

4. The gantry as claimed in claim 2,
wherein the gantry has a tilt drive configured to drive the tilting movement of the tilt frame about the tilt axis relative to the support frame, and
wherein a distance, from the tilt axis, of at least one of the proximity sensor or the reference mark is greater than a length of a lever arm of the tilt drive with respect to the tilt axis.

5. The gantry as claimed in claim 1,
wherein the proximity switch has a reference area with a first sub-area and a second sub-area, the first sub-area and the second sub-area arranged consecutively with respect to an angular distance about the tilt axis,
wherein the reference mark is arranged, with respect to the angular distance about the tilt axis, between the first sub-area and the second sub-area,
wherein the first sub-area and the second sub-area differ with respect to interaction with the proximity sensor such that the proximity switch assumes a first signal status when, with respect to the angular distance about the tilt axis, the proximity sensor is situated closer to the first sub-area than to the second sub-area, and such that the proximity switch assumes a second signal status, which differs from the first signal status, when, with respect to the angular distance about the tilt axis, the proximity sensor is situated closer to the second sub-area than to the first sub-area.

6. The gantry as claimed in claim 5,
wherein the first sub-area is in a form of a first circular arc about a center of a circle,
wherein the second sub-area is in a form of a second circular arc about the center of a circle, and
wherein the center of the circle lies on the tilt axis.

7. The gantry as claimed in claim 6,
wherein the gantry has a reference structure made of a material, to which the proximity switch reacts on the approach of said material to the proximity sensor,
wherein the reference structure has the first sub-area, and
wherein a recess is in the reference structure and forms the second sub-area.

8. The gantry as claimed in claim 5, wherein an edge of the first sub-area, which adjoins the second sub-area, forms the reference mark.

9. The gantry as claimed in claim 1, wherein the proximity switch is an inductive proximity switch.

10. The gantry as claimed in claim 1, wherein the proximity switch is an optical proximity switch.

11. The gantry as claimed in claim 10, wherein the optical proximity switch is in a form of a light barrier.

12. The gantry as claimed in claim 1,
wherein the gantry has a tilt drive configured to drive the tilting movement of the tilt frame about the tilt axis relative to the support frame, and
wherein a distance, from the tilt axis, of at least one of the proximity sensor or the reference mark is greater than a length of a lever arm of the tilt drive with respect to the tilt axis.

13. The gantry as claimed in claim 1,
wherein the proximity sensor is fixedly arranged relative to the tilt frame, and
wherein the reference mark is fixedly arranged relative to the support frame.

14. The gantry as claimed in claim 1,
wherein the proximity sensor is fixedly arranged relative to the support frame, and
wherein the reference mark is fixedly arranged relative to the tilt frame.

15. A computed tomography device having a gantry as claimed in claim 1.

16. A method comprising:
detecting an approach of a tilt angle to a reference angle via the proximity switch in the gantry as claimed in claim 1.

17. A gantry for a computed tomography device, the gantry comprising:
a support frame;
a tilt frame;
a tilt bearing;
a rotary frame;
a rotary bearing; and
a proximity switch;
wherein the rotary frame is arranged on the tilt frame and configured to rotate, via the rotary bearing, relative to the tilt frame about an axis of rotation,
wherein the tilt frame is arranged on the support frame and configured to tilt, via the tilt bearing, about a tilt axis relative to the support frame such that a tilt angle of the tilt frame relative to the support frame is changeable by a tilting movement of the tilt frame relative to the support frame, about the tilt axis, wherein the proximity switch has a proximity sensor and a reference mark, the reference mark configured to interact with the proximity sensor, wherein the proximity switch is coupled to the support frame and to the tilt frame such that the proximity switch is configured to react to an approach of the tilt angle to a reference angle, wherein the proximity switch has a reference area with a first sub-area and a second sub-area, wherein the gantry has a reference structure made of a material to which the proximity switch reacts on approach of said material to the proximity sensor, wherein the reference structure includes the first sub-area, and wherein a recess is in the reference structure and forms the second sub-area.

18. The gantry as claimed in claim 17, wherein the material is sheet metal.

19. The gantry as claimed in claim 17, wherein the proximity sensor and the reference mark are arranged offset relative to one another with respect to a direction parallel to the tilt axis, and wherein the proximity sensor and the reference mark are equally distant from the tilt axis.

\* \* \* \* \*